Figures 1, 2:
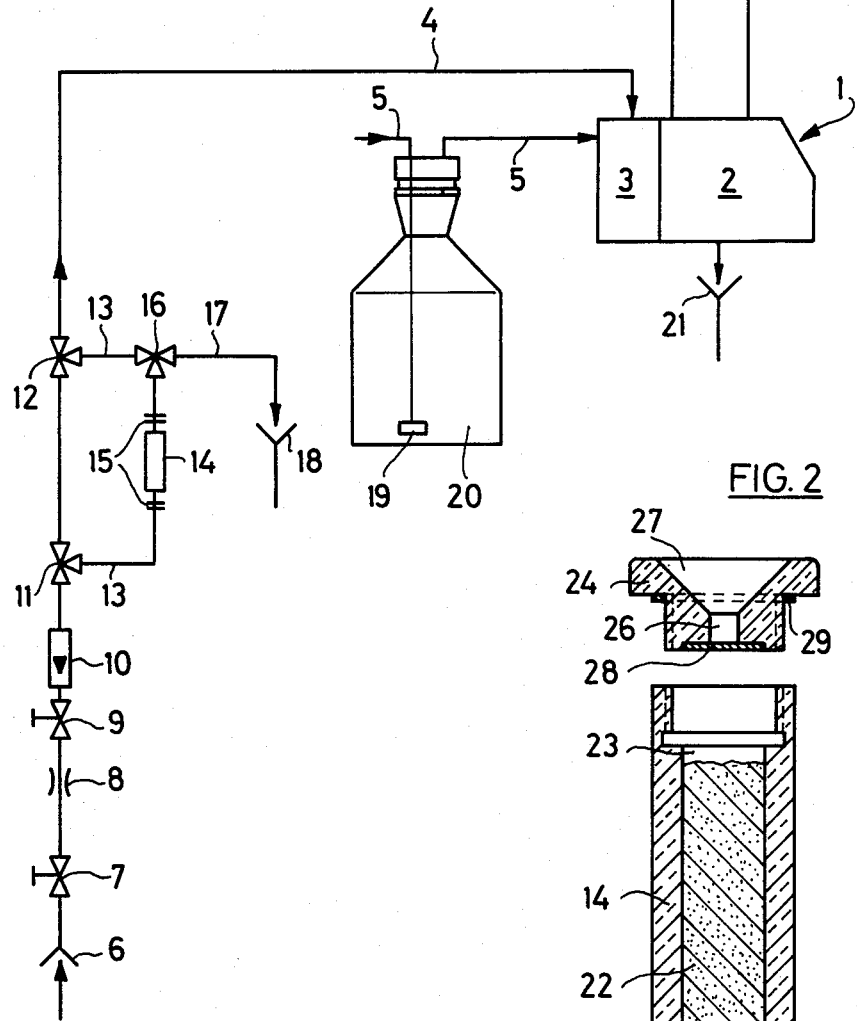

United States Patent [19]

Ertl et al.

[11] Patent Number: 4,625,543

[45] Date of Patent: Dec. 2, 1986

[54] METHOD AND DEVICE FOR CALIBRATING AN ANALYZER FOR MEASURING LOW ION ACTIVITY VALUES IN A SAMPLE STREAM

[75] Inventors: Stefan Ertl; Martin Jola, both of Hombrechtikon, Switzerland

[73] Assignee: Zellweger Uster Ltd., Uster, Switzerland

[21] Appl. No.: 753,460

[22] Filed: Jul. 10, 1985

[30] Foreign Application Priority Data

Jul. 18, 1984 [CH] Switzerland .......................... 3486/84

[51] Int. Cl.$^4$ ............................................. G01C 25/00
[52] U.S. Cl. .................................................... 73/1 G
[58] Field of Search ................. 73/1 R, 1 G; 324/438; 204/433; 436/163

[56] References Cited

U.S. PATENT DOCUMENTS 4,016,743  4/1977  Henderson et al. .................. 73/1 R
4,288,308  9/1981  Hach .............................. 324/438 X
4,350,675  9/1982  Drake ........................ 424/1
4,473,458  9/1984  Schwartz et al. ................ 73/1 R X

*Primary Examiner*—Jerry W. Myracle
*Attorney, Agent, or Firm*—Antonelli, Terry & Wands

[57] ABSTRACT

A sample stream is conditioned by the addition of reagents and the ion concentration is measured by means of a measuring system which can be connected to an arrangement for releasing an appropriate calibrating substance. The calibrating substance used is a soluble glass for the defined release of a known quantity of the ions to be measured, and the reference concentration is established directly in the sample stream. There is therefore no need for a calibrating solution or a metering pump for the latter, and disturbances due to the undesired transfer of impurities and reactive ions are avoided. The method is particularly suitable for the analysis of Na$^+$, the soluble glass being a sodium polyphosphate glass.

14 Claims, 2 Drawing Figures

METHOD AND DEVICE FOR CALIBRATING AN ANALYZER FOR MEASURING LOW ION ACTIVITY VALUES IN A SAMPLE STREAM

This invention relates to a method for calibrating an analyzer for measuring low ion activity values in a sample stream. In the analyzer, the sample stream is conditioned by the addition of reagents and the ion concentration is measured by means of a measuring system which can be connected to an arrangement for releasing the ions to be measured from an appropriate calibrating substance.

Methods of measuring low ion activities are used, for example, for measuring the sodium ion activity or the chloride ion activity in a stream of water. The determination of low ion activity values in a sample stream is limited by the fact that, due to the response of the electrode to $H^+$ and $OH^-$ ions, disturbances occur which lead to noticable measuring errors. Because $H^+$ and $OH^-$ ions are present in all aqueous sample streams, it is essential to adjust the pH with a conditioning agent before the electrochemical determination of low cation and anion activity values, in order to permit accurate measurement. When an acid is added as the conditioning agent, the pH is lowered by the removal of $OH^-$ ions from the sample stream, and when a base is added as the conditioning agent, the pH is raised by the removal of $H^+$ ions from the sample stream.

As the zero point and slope of the measuring system used to measure the ion activity (this system consisting of a measuring electrode and a reference electrode) are subject to drift over a prolonged period, regular calibration of the measuring system is necessary. This drift is caused, for example, by changes in the measuring electrode and in the diffusion potential of the reference electrode. For reasons which are known, the calibration is carried out near the range of the ion activity to be measured.

In known calibrating methods, the calibration is carried out with a calibrating solution which is added to the sample stream with the aid of a metering unit incorporating a metering pump, whereby a known concentration of the ions to be measured is produced in the sample stream.

Apart from the fact that the metering pump represents an additional and hence undesirable expense, calibration with a calibrating solution presents some difficulties in the measurement of low activities of the order of less than $10^{-6}$ in highly purified water, and makes very high demands on the preparation of the calibrating solution and the precision of the metering pump.

Now, an object of the invention is to provide a method for calibrating an analyzer for measuring low ion activity values in a sample stream, which requires neither a calibrating solution nor a special metering pump.

This object is achieved according to the invention by using, as a calibrating substance, a soluble glass for the defined release of a known quantity of the ions to be measured, and establishing the reference concentration directly in the sample stream.

Using the soluble glass and establishing the reference concentration directly in the sample stream dispenses with the need for either a calibrating solution or a metering pump and avoids disturbances due to the undesired transfer of impurities and reactive ions, which can never be totally excluded when using a calibrating solution.

The invention further relates to a device for carrying out the method, comprising a measuring cell, means, connected to the measuring cell, for introducing a sample stream and reagents, and an arrangement for calibrating the measuring cell.

The device according to the invention is characterized in that the calibrating arrangement has an insert with a soluble glass for releasing the ions to be measured into the sample stream.

Advantageous embodiments of the method according to the invention and of the device according to the invention are given in the following detailed description.

The invention is illustrated in greater detail with reference to an example and the accompanying drawings wherein:

FIG. 1 shows a flow chart of a system for measuring $Na^+$ activity with a calibrating arrangement according to the invention; and FIG. 2 shows a section through the calibrating arrangement of the system of FIG. 1, on an enlarged scale.

According to FIG. 1, the device for measuring the ion activity values, in the present case the $Na^+$ activity values, in a sample stream consists of a measuring cell 1 with a measuring part 2 and a mixing part 3 into which two lines 4 and 5 lead, the line 4 carrying the sample stream and the line 5 carrying the reagent used for conditioning the sample stream, which, in the present case of $Na^+$ measurement, is an alkalizing agent, e.g. ammonia.

In the direction of flow of the sample stream, the line 4 for the sample stream contains an inlet 6 for the sample stream, a hand-operated valve 7, a pressure regulator 8 for establish a constant pressure in the sample stream, a needle valve 9 for establishing the required flow rate, a flowmeter 10 and two reversing valves 11 and 12 which enable the sample stream to be routed, as required, through a by-pass 13 for calibrating the device.

The by-pass 13 contains a calibrating arrangement 14 in the form of a calibrating cartridge which can be connected manually into the by-pass 13 by means of quick-locking couplers 15, and also contains a reversing valve 16 from which a line 17 leads to an outlet 18.

Air is sucked through the line 5 for the alkalizing agent and is passed through a glass frit 19 in a vessel 20 containing $NH_4OH$, the air thereby being saturated with $NH_3$. The air saturated with $NH_3$, which thus constitutes the alkalizing agent, is thoroughly mixed in the mixing part 3 of the measuring cell 1 with the sample stream from the line 4, the pH of the sample stream thereby rising to a value above 10. The mixture of sample stream and $NH_3$-saturated air then flows through the measuring part 2 and ultimately into an outlet 21.

The measuring part 2 of the measuring cell 1 essentially contains a measuring unit or system comprising a sodium-selective measuring electrode and an Ag/AgCl reference electrode. The mixture of sample stream and $NH_3$-saturated air flows past the measuring electrode; whereas the reference electrode is immersed in a suitable electrolyte, for example, KCl or LiCl of a specific concentration. Using these two electrodes affords the potentiometric measurement of $Na^+$ ions. The measuring cell 1 per se, is described in the Swiss Application No. 3416/84-2 filed on July 13, 1984, in the name of the Assignee of the present patent application.

Moreover, in respect of the system shown in FIG. 1, reference is made to the SODIMAT Na+ analyzer manufactured by the firm POLYMETRON, a subsidiary of ZELLWEGER USTER AG, and marketed throughout the world.

Due to changes in the sodium-selective measuring electrode and in the diffusion potential of the reference electrode, the zero point and slope of the measuring unit are subject to drift over a prolonged period, which makes it necessary to calibrate the unit periodically. For reasons which are known, the calibration is preferably carried out near the range of the sodium ion activity to be measured and has hitherto been carried out by means of a suitable calibrating solution, which has presented some difficulties in the measurement of low activities of the order of less than $10^{-6}$ in highly purified water, because very high demands were made on the preparation of the calibrating solution and the precision of the metering arrangement for adding it to the sample stream.

Now, with the calibrating arrangement 14 located in the by-pass 13, the reference concentration can be established directly in the sample stream without the need for a calibrating solution, thereby avoiding disturbances due to the undesired transfer of impurities and/or reactive ions.

According to FIG. 2, the calibrating arrangement 14 consists of a calibrating cartridge or container made of a transparent material such as Plexiglas, which has a chamber 23 containing a calibrating substance 22. Fitting into the chamber 23, the calibrating cartridge 14 has a top part and a bottom part, 24 and 25 respectively, one of which, in the present case the top part 24, is screwed onto the calibrating cartridge 14. FIG. 2 shows the top part 24 unscrewed. The top and bottom parts 24 and 25 each have a central bore 26 and an adapter cone 27 formed thereto, the adapter cones being provided for engagement with the quick-locking couplers 15 (FIG. 1). A filter disc 28 made of polyamid is inserted between each of the bores 26 and the chamber 23 and prevents the calibrating substance 22 from escaping out of the chamber 23. The top part 24 and the remaining part of the calibrating cartridge 14 are sealed by means of a seal 29 formed of rubber.

The calibrating substance 22 consists of a water-soluble glass of particulate or granular form, which releases sodium ions. Glasses of this type have been known hitherto for medical applications or applications associated with weather-resistant paints and are described, for example, in U.S. Pat. No. 4,350,675. The glass used as the calibrating substance 22 in the present case is a sodium polyphosphate glass which, on contact with the aqueous sample stream, releases a defined quantity of sodium into this stream at a known temperature. As the flow rate of the sample stream is also known, there is a defined sodium concentration in this stream. A glass of this type is described in the British patent application "Water-soluble composition for preparing analytical solutions" in the name of International Standard Electrical Corp., of 18th July 1984.

Thus, the sodium ion activity established in the sample stream, when the sample stream is routed through the calibrating cartridge 14 by means of the by-pass 13 (FIG. 1), is dependent on the temperature, the flow rate of the sample stream and the composition of the water-soluble sodium polyphosphate glass. For example, at a flow rate of 3.5 liters/hour and at 20° C., with a glass having the following composition: CaO: 50.4 mol %; Na$_2$O: 2.5 mol %; P$_2$O$_5$: 47.1 mol %; the Na+ concentration is 3 ppb.

The desired calibrating cartridge 14 is manually connected into the by-pass 13 (FIG. 1) by means of the quick-locking couplers 15; in the case where the calibrations are carried out manually, the by-pass does not need to have the reversing valve 16, the line 17 and the outlet 18. Now, if the reversing valves 11 and 12 are switched in such a way that the direct connection between them is blocked, the sample stream is routed through the calibrating cartridge 14, affording calibration of the system. After calibration, the reversing valves 11 and 12 are switched to the appropriate positions and the system of FIG. 1 is ready for carrying out a measurement.

The calibration can be carried out each time with a single calibrating cartridge 14 with the appropriate Na+ concentration printed on it and accompanied by a temperature curve, which can of course also be integrated into the software of the system. The concentration printed on the calibrating cartridge 14 is established by means of the zero point of the measuring unit on the assumption that the slope of the measuring unit has remained constant, that the concentration produced by the calibrating cartridge 14 is at least 50 to 100 times higher than the sample concentration, and that the temperature and flow rate correspond to the specified parameters.

The accuracy of this calibration, which is already adequate in practice for all common requirements, can be increased by first purifying the sample stream to "zero" sodium by means of an ion exchange cartridge which is placed upstream of the calibrating cartridge and only then routing it through the calibrating cartridge 14. The indicated concentration value then agrees exactly. If the slope of the measuring unit is also eventually established again, this can be done by means of a second calibrating cartridge 14 of a different concentration.

This last variant of the calibration with two calibrating cartridges 14 of different concentrations is preferentially used and, in this case, the by-pass 13 (FIG. 1) has two parallel branches each containing a calibrating cartridge 14. If the zero point and slope are then calculated by means of a microcomputer in accordance with the known addition method with iteration, the calibration can be carried out without knowing the initial Na+ content of the sample stream.

The use of a microcomputer enables the calibration process to be automated, two calibrating cartridges of different concentrations being inserted for a sufficient length of time. For this automatic calibration, it is advantageous if the by-pass 13 is designed according to FIG. 1, i.e., has the reversing valve 16 and the line 17 leading to the outlet 18. The reversing valves 11, 12 and 16 can then be actuated by machine and are controlled by the microcomputer. The procedure for instantaneous calibration is as follows: in the normal measuring mode of the system, where the direct connection between the reversing valves 11 and 12 is open, a small part of the sample stream is routed through the by-pass by means of the reversing valve 11 and flows through the calibrating cartridges 14, which do not then become dry and are thus always ready for calibration without delay. In the measuring mode of the system, the reversing valve 16 then routes this part of the sample stream from the calibrating cartridge 14 through the line 17 to the outlet 18.

For this automated calibration, it is advantageous if the polyphosphate glass consists of small rectangular chips (length 5-30 millimeters, cross section 0.1-5 sq.millimeters) so that the surface change occurring when the chips dissolve remains small. It is even more advantageous if the polyphosphate glass consists of one or more small tubes of same size like chips which are arranged in the longitudinal direction of the chamber 23 and around which the sample stream flows, on its or their outer surface and inner surface. In this case, the corresponding surface changes cancel each other out and the surface area remains constant.

Although the method according to the invention is described above in relation to an $Na^+$ analyzer, this is not to be understood as limiting, since it is clear to those skilled in the art that the method can also be used for the measurement of other cation and anion activity as well as for other measurements, for example, for the measurement of free chlorine, for which it would simply be necessary to use a water-soluble glass of a different composition.

While we have shown and described several embodiments in accordance with the present invention, it is understood that the same is not limited thereto but is susceptible of numerous changes and modifications as known to one having ordinary skill in the art and we therefore do not wish to be limited to the details shown and described herein, but intend to cover all such modifications as are encompassed by the scope of the appended claims.

We claim:

1. A method for calibrating an analyzer for measuring low ion activity values in a sample stream, wherein in the analyzer the sample stream is conditioned by the addition of reagents and the ion concentration is measured by means of a measuring system, which comprises introducing ions to be measured in a given concentration into the sample stream by passing the stream over an appropriate calibrating substance which releases the ions into said stream, said substance comprising a water soluble glass for the defined release of a known quantity of the ions to be measured, and establishing a reference concentration directly in the sample stream.

2. The method according to claim 1, wherein two calibrating substances of different concentrations are used in a parallel arrangement.

3. The method according to claim 1 for measuring the activity value of $Na^+$ ions, wherein said water-soluble glass is a sodium polyphosphate glass.

4. The method according to claim 3, wherein the sodium polyphosphate glass has the following composition: CaO: 45 to 55 mol %, $Na_2O$: 0.5 to 10 mol %, $P_2O_5$: 45 to 55 mol %.

5. The method according to claim 1, further comprising purifying the sample stream to a zero concentration of the ions to be measured, prior to introducing the ions to be measured in a given concentration into the sample stream, by passing the sample stream through an ion exchange resin placed upstream of the calibrating substance.

6. A device for measuring low ion activity values in a sample stream conditioned by the addition of reagents comprising a measuring cell, means, connected to the cell, for introducing the sample stream and the reagents, and an arrangement for calibrating the measuring cell comprising a container retaining a water-soluble glass for releasing the ions to be measured into the sample stream, said container having an inlet and outlet means for allowing the sample stream to pass over the water-soluble glass.

7. The device according to claim 6, wherein the means for introducing the sample stream including by-pass means through which the sample stream can be routed as required, and the container with the water soluble glass is located in said by-pass means.

8. The device according to claim 7, wherein the by-pass means includes two parallel branches each containing a container with a water soluble glass of a different concentration.

9. The device according to claim 7 further comprises means, when the device is in the measuring mode, for allowing a small portion of the sample stream to flow through the by-pass means, said portion being led from the by-pass means through a line to an outlet for discharge from the system.

10. The device according to claim 6, wherein said container comprises a cylindrical cartridge defining a chamber for the water soluble glass and a top closure element and a bottom closure element that fit into an end of the cartridge to seal the chamber, each closure element having an opening for the passage of the sample stream through said soluble glass.

11. The device according to claim 10, wherein each opening is sealed, at its end against the chamber by a filter disc, and opens out, at its other end, into an adapter cone provided for engagement with a quick-locking coupler.

12. The device according to claim 10, wherein the chamber contains the water soluble glass in particulate or granular form.

13. The device according to claim 10, wherein the chamber contains the water soluble glass in the form of small chips, the length and width of which are large compared with the thickness.

14. The device according to claim 10, wherein the chamber contains the water soluble glass in the form of small tubes which are arranged in the longitudinal direction of the chamber and around which the sample stream flows, both on the outer surface and on the inner surface thereof.

* * * * *